United States Patent
Nagai et al.

(10) Patent No.: US 9,945,784 B2
(45) Date of Patent: Apr. 17, 2018

(54) FLUORESCENT PROTEIN

(71) Applicant: OSAKA UNIVERSITY, Suita-shi, Osaka (JP)

(72) Inventors: Takeharu Nagai, Osaka (JP); Dhermendra Kumar Tiwari, Singapore (SG); Yoshiyuki Arai, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/021,371

(22) PCT Filed: Sep. 11, 2014

(86) PCT No.: PCT/JP2014/074121
§ 371 (c)(1),
(2) Date: Mar. 11, 2016

(87) PCT Pub. No.: WO2015/037674
PCT Pub. Date: Mar. 19, 2015

(65) Prior Publication Data
US 2016/0231248 A1    Aug. 11, 2016

(30) Foreign Application Priority Data
Sep. 13, 2013   (JP) .................................. 2013-191058

(51) Int. Cl.
| | |
|---|---|
| *G01N 21/64* | (2006.01) |
| *C07K 14/435* | (2006.01) |
| *C07K 14/00* | (2006.01) |
| *C07K 14/47* | (2006.01) |
| *C12Q 1/02* | (2006.01) |
| *G01N 33/50* | (2006.01) |

(52) U.S. Cl.
CPC ......... *G01N 21/6486* (2013.01); *C07K 14/00* (2013.01); *C07K 14/435* (2013.01); *C07K 14/47* (2013.01); *C07K 14/4716* (2013.01); *C12Q 1/02* (2013.01); *G01N 33/5005* (2013.01); *C07K 2319/00* (2013.01); *C07K 2319/21* (2013.01)

(58) Field of Classification Search
None
See application file for complete search history.

(56) References Cited

U.S. PATENT DOCUMENTS

2009/0155888 A1    6/2009 Miyawaki et al.

FOREIGN PATENT DOCUMENTS

WO    2005/113772 A1    12/2005

OTHER PUBLICATIONS

International Search Report dated Dec. 16, 2014, issued in counterpart International Application No. PCT/JP2014/074121 (2 pages).
Andresen et al., "Photoswitchable fluorescent proteins enable monochromatic multilabel imaging and dual color fluorescence nanoscopy", Nature Biotechnology, Aug. 24, 2008, pp. 1035-1040, vol. 26, No. 9, cited in the ISR (6 pages).
Brakemann et al., "Molecular Basis of the Light-driven Switching of the Photochromic Fluorescent Protein Padron", The Journal of Biological Chemistry, May 7, 2010, pp. 14603-14609, vol. 285, No. 19, cited in the Specification and the ISR (8 pages).
Brakemann et al., "A reversibly photoswitchable GFP-like protein with fluorescence excitation decoupled from switching", Nature Biotechnology, Oct. 2011, vol. 29, No. 10 (9 pages).
Grotjohann et al., "rsEGFP2 enables fast RESOLFT nanoscopy of living cells", Elife, 2012 (14 pages).
Grotjohann et al., "Diffraction-unlimited all-optical imaging and writing with a photochromic GFP", Nature, Oct. 13, 2011, pp. 204-208, vol. 478 (5 pages).
S. Gayda, et al. "Mechanistic Insights into Reversible Photoactivation in Proteins of the GFP Family", Biophysical Journal, vol. 103, Dec. 2012, No. 12, pp. 2521-2531. Cited in the Extended (supplementary) European Search Report dated Jan. 23, 2017.
Extended (supplementary) European Search Report dated Jan. 23, 2017, issued in counterpart European Patent Application No. 14843850.0. (6 pages).

*Primary Examiner* — Suzanne M Noakes
(74) *Attorney, Agent, or Firm* — Westerman, Hattori, Daniels & Adrian, LLP

(57) ABSTRACT

Provided is a fluorescent protein that has a fast photoswitching speed and a high photostability and that switches from a non-fluorescent state to a fluorescent state by being irradiated with light for fluorescence excitation and switches from a fluorescent state to a non-fluorescent state by being irradiated with light having a specific wavelength that does not cause fluorescence excitation. The present invention relates to (a) A protein having an amino acid sequence of Sequence ID No. 1. (b) A protein that has an amino acid sequence of Sequence ID No. 1 in which one to several amino acids are deleted, substituted, and/or added.

6 Claims, 5 Drawing Sheets c d e f
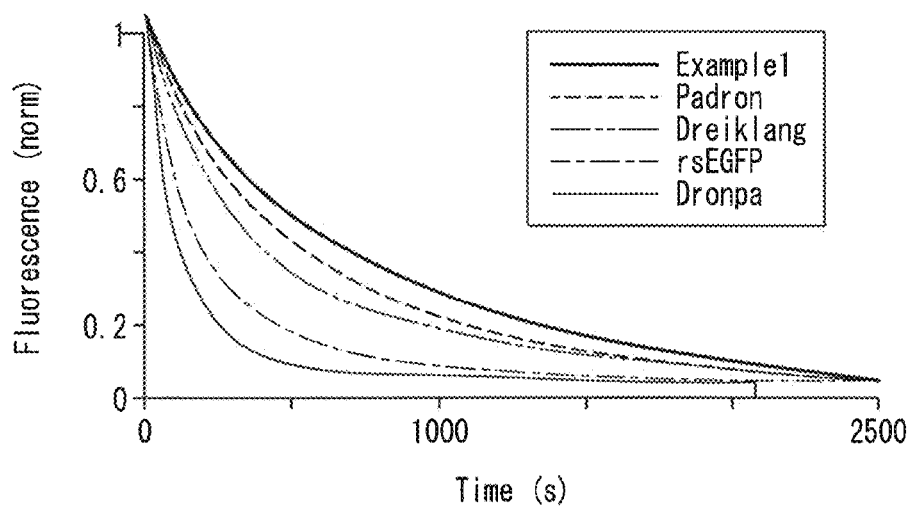
g
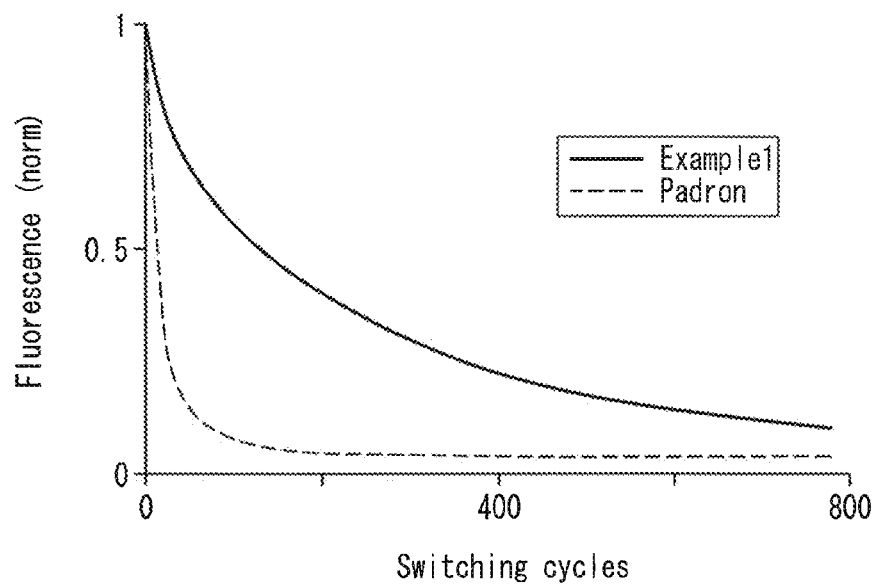
FIG. 1-4

SEQUENCE LISTING

```
<160> NUMBER OF SEQ ID NOS: 4

<210> SEQ ID NO 1
<211> LENGTH: 224
<212> TYPE: PRT
<213> ORGANISM: Artificial Sequence
<220> FEATURE:
<223> OTHER INFORMATION: New CS-RSFP (cooperatively switching reversibly
      photoswitchable fluorescent protein)

<400> SEQUENCE: 1
```

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Met Ala Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Ile Tyr Glu
            85                  90                  95

Asp Gly Gly Ile Cys Ile Ala Thr Asn Asp Ile Thr Leu Asp Gly Asp
        100                 105                 110

Cys Tyr Ile Tyr Glu Ile Arg Phe Asp Gly Val Asn Phe Pro Ala Asn
    115                 120                 125

Gly Pro Val Met Gln Lys Arg Thr Val Lys Trp Glu Pro Ser Thr Glu
130                 135                 140

Lys Leu Tyr Val Arg Asp Gly Val Leu Lys Ser Asp Gly Asn Tyr Ala
145                 150                 155                 160

Leu Ser Leu Glu Gly Gly Gly His Tyr Arg Cys Asp Ser Lys Thr Thr
            165                 170                 175

Tyr Lys Ala Lys Lys Val Val Gln Leu Pro Asp Tyr His Asp Val Val
        180                 185                 190

His His Ile Glu Ile Lys Ser His Asp Arg Asp Tyr Ser Asn Val Asn
    195                 200                 205

Leu His Glu His Ala Glu Ala His Ser Gly Leu Pro Arg Gln Ala Lys
210                 215                 220

```
<210> SEQ ID NO 2
<211> LENGTH: 224
```

```
<212> TYPE: PRT
<213> ORGANISM: Artificial Sequence
<220> FEATURE:
<223> OTHER INFORMATION: Padron, CS-RSFP (cooperatively switching
      reversibly photoswitchable fluorescent protein)

<400> SEQUENCE: 2

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
                20                  25                  30

Pro Phe Glu Gly Lys Gln Ser Met Asp Leu Lys Val Lys Glu Gly Gly
            35                  40                  45

Pro Leu Pro Phe Ala Tyr Asp Ile Leu Thr Met Ala Phe Cys Tyr Gly
        50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Ile Tyr Glu
                85                  90                  95

Asp Gly Gly Ile Cys Asn Ala Thr Asn Asp Ile Thr Leu Asp Gly Asp
            100                 105                 110

Cys Tyr Ile Tyr Glu Ile Arg Phe Asp Gly Val Asn Phe Pro Ala Asn
        115                 120                 125

Gly Pro Val Met Gln Lys Arg Thr Val Lys Trp Glu Leu Ser Thr Glu
    130                 135                 140

Lys Leu Tyr Val Arg Asp Gly Val Leu Lys Ser Asp Gly Asn Tyr Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Ser Val Asp
            180                 185                 190

His His Ile Glu Ile Lys Ser His Asp Lys Asp Tyr Ser Asn Val Asn
        195                 200                 205

Leu His Glu His Ala Glu Ala His Ser Glu Leu Pro Arg Gln Ala Lys
    210                 215                 220

<210> SEQ ID NO 3
<211> LENGTH: 672
<212> TYPE: DNA
<213> ORGANISM: Artificial Sequence
<220> FEATURE:
<223> OTHER INFORMATION: New CS-RSFP (cooperatively switching reversibly
      photoswitchable fluorescent protein)

<400> SEQUENCE: 3
atgagtgtga ttaaaccaga catgaagatc aagctgcgta tggaaggcgc tgtaaatgga    60
cacccgttcg cgattgaagg agttggcctt gggaagcctt tcgagggaaa acagagtatg   120
gaccttaaag tcaaagaagg cggacctctg cctttcgcct atgacatctt gacaatggcc   180
ttctgttacg gcaacagggt attcgccaaa tacccagaaa atatagtaga ttatttcaag   240
cagtcgtttc ctgagggcta ctcttgggaa cgaagcatga tttacgaaga cgggggcatt   300
tgtatcgcga caacgacat aaccctggat ggtgactgtt atatctatga aattcgattt   360
gatggtgtga actttcctgc caatggtcca gttatgcaga agaggactgt gaaatgggag   420
ccatccactg agaaattgta tgtgcgtgat ggagtgctga gagcgatgg caattacgct   480 ctgtcgcttg aaggaggtgg ccactaccga tgtgactcca aaactactta taaagctaag   540
```

```
aaggttgtcc agttgccaga ctatcacgat gtggtccacc acattgagat taaaagccac    600
gacagagatt acagtaatgt taatctgcat gagcatgccg aagcgcattc tgggctgccg    660
aggcaggcca ag                                                        672

<210> SEQ ID NO 4
<211> LENGTH: 17
<212> TYPE: PRT
<213> ORGANISM: Artificial Sequence
<220> FEATURE:
<223> OTHER INFORMATION: Amino acid linker sequence

<400> SEQUENCE: 4

Gly Gly Ser Gly Gly Ser Gly Gly Ser Gly Gly Ser Gly Gly Gln Phe
                5                   10                  15
Gly
```

FLUORESCENT PROTEIN

TECHNICAL FIELD

The present disclosure relates to a fluorescent protein.

BACKGROUND ART

Fluorescent proteins have been facilitating live cell imaging, and thus various structures in cells and various functions thereof have been clarified. In recent years, a super-resolution method using fluorescent proteins whose fluorescence can be reversibly photo-switched (reversibly photo-switchable fluorescent protein, RSFP) has been developed, and thus imaging can be performed beyond the diffraction limit of an optical microscope. Examples of the RSFPs include 1) a negative photo-switchable type (e.g., Dronpa (Patent Document 1) and rsEGFP) that switches from a non-fluorescent state to a fluorescent state by being irradiated with light having a specific wavelength that does not cause fluorescence excitation and switches from a fluorescent state to a non-fluorescent state by being irradiated with light for fluorescence excitation; 2) a positive photo-switchable type (e.g., Padron (Non-Patent Document 1)) that switches from a non-fluorescent state to a fluorescent state by being irradiated with light for fluorescence excitation and switches from a fluorescent state to a non-fluorescent state by being irradiated with light having a specific wavelength that does not cause fluorescence excitation; and 3) a type (e.g., Dreiklang) in which wavelengths for the switching on/off of the fluorescence and a fluorescence excitation wavelength are entirely independent of each other.

PRIOR ART DOCUMENTS

Patent Document

[Patent Document 1] WO 2005/113772

Non-Patent Document

[Non-Patent Document 1] Tanja Brakemann et al, J. Biol. Chem. 2010, 285: 14603-14609

DISCLOSURE OF INVENTION

Problem to be Solved by the Invention

In the case of the negative photo-switchable type, which switches from a non-fluorescent state to a fluorescent state by being irradiated with light having a specific wavelength that does not cause fluorescence excitation and switches from a fluorescent state to a non-fluorescent state by being irradiated with light for fluorescence excitation, the fluorescence is switched off by the irradiation with excitation light for fluorescence observation, and, a problem arises in that the fluorescence is switched off during the fluorescence observation and in that it is difficult to rapidly switch the fluorescence while a high S/N ratio is maintained. Moreover, in the case of the positive photo-switchable type, which switches from a non-fluorescent state to a fluorescent state by being irradiated with light for fluorescence excitation and switches from a fluorescent state to a non-fluorescent state by being irradiated with light having a specific wavelength that does not cause fluorescence excitation, there is a problem in that the photo-switching speed is slower and the photostability is lower compared with the negative photo-switchable type.

The present disclosure provides a fluorescent protein that has a fast photo-switching speed and a high photostability and that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

Means for Solving the Problem

In one or more embodiments, the present disclosure relates to a fluorescent protein indicated in (a) or (b) below.

(a) A protein having an amino acid sequence of Sequence ID No. 1.

(b) A protein that has an amino acid sequence of Sequence ID No. 1 in which one to several amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

Effects of the Invention

With the present disclosure, in one embodiment, it is possible to provide a fluorescent protein in which the photo-switching speed and the photostability are improved and the number of photo-switching cycles increases. Moreover, with the fluorescent protein of the present disclosure, in one or more embodiments, a time resolution increases, and thus time-lapse observation can be performed for a long period of time. Furthermore, with the fluorescent protein of the present disclosure, in one or more embodiments, the resolution of super-resolution imaging can be improved.

BRIEF DESCRIPTION OF DRAWINGS

FIG. 1-1 to FIG. 1-4 are diagrams illustrating examples of characterization results of a fluorescent protein of Example 1. FIG. 1-1a shows changes in an irradiation-dependent absorbance spectrum of the fluorescent protein of Example 1 at pH 7.4.

FIG. 1-2b shows changes in an irradiation-dependent absorbance spectrum of Padron at pH 7.4.

FIG. 1-3c shows a fluorescence emission spectrum and an excitation spectrum of the fluorescent protein of Example 1. FIG. 1-3d shows kinetics of photo-switching on/off of the fluorescent protein of Example 1 and Padron. FIG. 1-3e shows examples of continuous photo-switching of the fluorescent protein of Example 1 and Padron.

FIG. 1-4f shows examples of photobleaching kinetics of the fluorescent protein of Example 1, Padron, Dreiklang, rsEGFP, and Dronpa. Regarding the photobleaching of the protein of Example 1 and Dreiklang, a 488-nm laser beam (7.1 kW/cm$^2$) was applied, and the fluorescence was recorded. Regarding the photobleaching of rsEGFP and Dronpa, a 405-nm laser beam (29.1 kW/cm$^2$) as well as a 488-nm laser beam (7.1 kW/cm$^2$) were applied, and the fluorescence was recorded. FIG. 1-4g shows examples of photobleaching promoted by photo-switching.

FIG. 2 shows examples of PALM imaging results of HeLa cells expressing a fusion protein of the fluorescent protein of Example 1 and β-actin. FIG. 2a is a wide-field image of the fusion protein. FIGS. 2b, 2c, and 2d are enlarged views of boxes 1, 2, and 3 in FIG. 2a, respectively. FIG. 2e is a fluorescence line profile normalized along a solid line in FIG. 2c. FIG. 2f is a PALM image of the fusion protein. FIGS. 2g, 2h, and 2j are enlarged views of portions in FIG. 2f that correspond to boxes 1, 2, and 3 in FIG. 2a, respectively. FIG. 2j is a fluorescence line profile normalized along a solid line in FIG. 2h. Scale bars in FIGS. 2a and 2f indicate 5 μm. All scale bars in the enlarged views indicate 500 nm.

DESCRIPTION OF THE INVENTION

Figure 1:
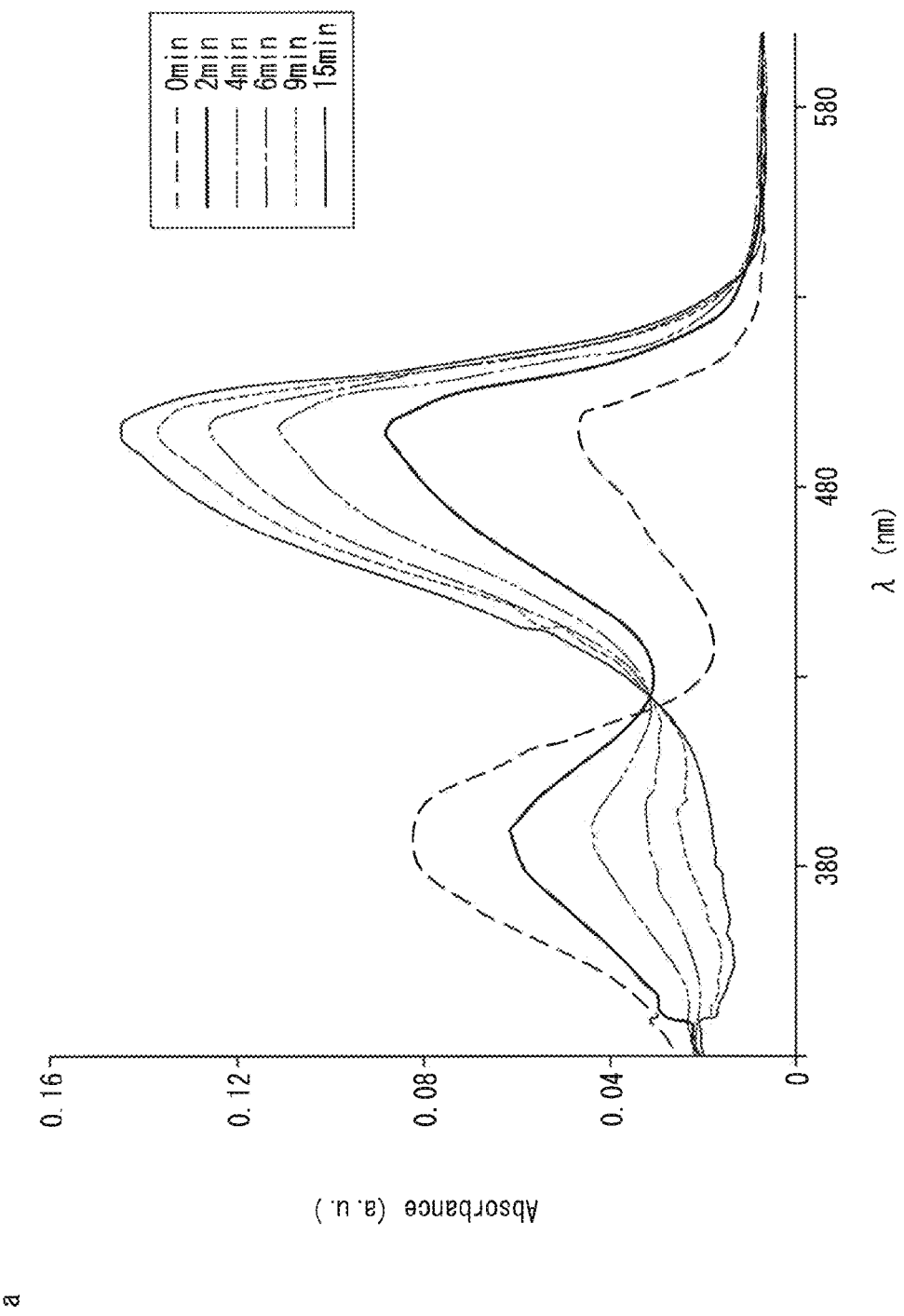

In order to develop a fluorescent protein that has a fast photo-switching speed and a high photostability, and that has a fluorescence property of exhibiting a photochromism effect, first, the inventors of the present invention focused on Padron (having an amino acid sequence of Sequence ID No. 2), which is a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation, out of known RSFPs. The present disclosure is based on the finding that introducing seven mutations (N102I, L141P, F173S, S190D, D192V, K202R, and E218G) into the amino acid sequence of Padron makes it possible to obtain a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation, the fluorescent protein having a fast photo-switching speed and a high photostability, and the number of cycles (reverse cycles) of switching from a non-fluorescent state to a fluorescent state and/or from a fluorescent state to a non-fluorescent state being higher.

In one or more embodiments, the photo-switching speed of the fluorescent protein of the present disclosure is improved. In another one or more embodiments, the photo-switching speed of the fluorescent protein of the present disclosure is faster than that of Padron. In live cell imaging, a target to be observed performs movements such as Brownian diffusion and directed displacement. If the target to be observed performs movements while one image is being taken, spatial resolution decreases. Therefore, the improved photo-switching speed makes it possible to improve the spatial resolution of imaging.

In one or more embodiments, the photostability of the fluorescent protein of the present disclosure is improved. In another one or more embodiments, the photostability of the fluorescent protein of the present disclosure is higher than that of Padron. When bleached (faded), the fluorescent protein emits no fluorescence and cannot be observed. Therefore, the longer it takes until the fluorescent protein is bleached, that is, the higher the photostability is, the longer the period of time for which the fluorescent protein can be observed is.

In one or more embodiments, the number of photo-switching cycles of the fluorescent protein of the present disclosure, that is, the number of cycles of photo-switching from a non-fluorescent state to a fluorescent state and/or from a fluorescent state to a non-fluorescent state that can be performed until the fluorescent protein is bleached increases.

In another one or more embodiments, the number of photo-switching cycles of the fluorescent protein of the present disclosure increases compared with that of Padron. When bleached, the fluorescent protein emits no fluorescence and cannot be observed. Therefore, the higher the number of on/off cycles of photo-switching that can be performed until the fluorescent protein is bleached is, that is, the higher the number of photo-switching cycles is, the longer the period of time for which the fluorescent protein can be observed is.

In one or more embodiments, the fluorescent protein of the present disclosure has a fast photo-switching speed and a high photostability. Moreover, in another one or more embodiments, the number of photo-switching cycles of the fluorescent protein of the present disclosure further increases.

The fluorescent protein of the present disclosure is a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation, and the fluorescence is stably in an on state even during the irradiation with excitation light. Therefore, in one or more embodiments, sufficient signals can be detected within a detector exposure time.

In one or more embodiments, the fluorescent protein of the present disclosure is a protein that is expressed in a fluorescent state. The term "expressed in a fluorescent state" means that a protein emits fluorescence in the initial phase of expression in a cell. On the other hand, Padron is a protein that is expressed in a non-fluorescent state. The fluorescent protein of the present disclosure is expressed in a fluorescent state, and therefore, in one or more embodiments, it is easy to check which cells express the fluorescent protein of the present disclosure.

Fluorescent Protein of the Present Disclosure

An aspect of the present disclosure relates to a fluorescent protein (also referred to as the "fluorescent protein of the present disclosure" hereinafter) indicated in (a) or (b) below.

(a) A protein having an amino acid sequence of Sequence ID No. 1.

(b) A protein that has an amino acid sequence of Sequence ID No. 1 in which one to several amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

In one or more embodiments, the fluorescence property of the protein having an amino acid sequence of Sequence ID No. 1 in which one to several amino acids are deleted, substituted, and/or added may be the same as or different from that of the protein having an amino acid sequence of Sequence ID No. 1. In one or more embodiments, the term "one to several" in the present disclosure includes 1 to 50, 1 to 40, 1 to 35, 1 to 30, 1 to 25, 1 to 20, 1 to 15, 1 to 10, 1 to 9, 1 to 8, 1 to 7, 1 to 6, 1 to 5, 1 to 4, 1 to 3, 1 to 2, or 1.

In one or more embodiments, the term "fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation" in the present disclosure means a positive photoswitchable type fluorescent protein that can be reversibly photo-switched. In one or more embodiments, the term "photo-switchable type fluorescent protein that can be reversibly photo-switched" in the present disclosure means a protein in which turning-on and turning-off of fluorescence can be controlled by the two types of irradiation with light having different wavelengths, and an on state and an off state can be repeatedly switched.

In one or more embodiments, the fluorescent protein of the present disclosure may be a protein synthesized by chemical synthesis or a recombinant protein produced with a gene recombination technique. In one or more embodiments, an example of the method for producing a protein with a gene recombination technique is a method for producing a protein using a host transformed by an expression vector including a gene coding for the fluorescent protein of the present disclosure.

In one or more embodiments, regarding the fluorescent protein of the present disclosure, the protein indicated in (b) above is a protein that is expressed in a fluorescent state.

In one or more embodiments, the fluorescent protein of the present disclosure is a fusion protein in which the fluorescent protein indicated in (a) or (b) above is fused to another protein or peptide, and in which the fluorescent protein moiety can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation. In one or more embodiments, the fluorescent protein of the present disclosure is a fusion protein in which the fluorescent protein moiety is expressed in a fluorescent state.

In non-limiting one or more embodiments, the protein to be connected to the fluorescent protein indicated in (a) or (b) above in the fusion protein includes a signal sequence, an expression tag, and a protein (a linker sequence as necessary).

The fluorescent protein of the present disclosure has a fast photo-switching speed and allows the fluorescence to be repeatedly read out. Therefore, in one or more embodiments, the fluorescent protein of the present disclosure can be used in super-resolution imaging, a super-high density optical memory, or hypersensitive fluorescent imaging. The fluorescent protein of the present disclosure allows photo-switching on/off of the fluorescence to be collaboratively repeated. Therefore, in one or more embodiments, the diffusion of molecules in a cell can be measured with a FDAP method. Moreover, in one or more embodiments, the fluorescent protein of the present disclosure can be used as a fluorescent function indicator, a luminescent protein, and a luminescent function indicator.

DNA of the Present Disclosure

An aspect of the present disclosure relates to DNA coding for the fluorescent protein of the present disclosure. Moreover, another aspect of the present disclosure relates to DNA (also referred to as "DNA of the present disclosure" hereinafter) that codes for a protein indicated in any of (a) to (c) below or that is indicated in (d) or (e) below.

(a) A protein having an amino acid sequence of Sequence ID No. 1.

(b) A protein that has an amino acid sequence of Sequence ID No. 1 in which one to several amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

(c) A fusion protein to which the protein indicated in (a) or (b) above is fused, and in which the protein moiety can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

(d) DNA having a base sequence of Sequence ID No. 3.

(e) DNA having a base sequence coding for a protein that has an amino acid sequence based on the base sequence of Sequence ID No. 3 in which one to several amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

In one or more embodiments, the DNA of the present disclosure is DNA from which the protein indicated in (b), (c), and (e) above is expressed in a fluorescent state.

In one or more embodiments, with the DNA of the present disclosure, the fluorescent protein of the present disclosure can be expressed and produced by introducing a recombinant vector including the DNA of the present disclosure into a host. In one or more embodiments, the DNA of the present disclosure can be manufactured with PCR using a specific primer, a phosphoamidite method, or the like.

Vector of the Present Disclosure

An aspect of the present disclosure is a vector allowing the fluorescent protein of the present disclosure to be expressed. In one or more embodiments, the vector of the present disclosure is a vector including the DNA of the present disclosure. In one or more embodiments, the vector of the present disclosure can be obtained by inserting the DNA of the present disclosure into an appropriate vector. There is no particular limitation on the vector into which the DNA of the present disclosure is to be inserted as long as the vector can replicate in a host, and examples thereof include a plasmid and a phage in one or more embodiments.

In one or more embodiments, examples of the plasmid include a plasmid derived from *Escherichia coli*, a plasmid derived from *Bacillus subtilis*, and a plasmid derived from yeast.

Transformant of the Present Disclosure

An aspect of the present disclosure relates to a transformant expressing the fluorescent protein of the present disclosure. In one or more embodiments, the transformant of the present disclosure is a cell expressing the fluorescent protein of the present disclosure, or a tissue, an organ or an organism in which the cell is included. Moreover, in one or more embodiments, the present disclosure relates to a transformant including the DNA or the recombinant vector of the present disclosure. In one or more embodiments, the transformant of the present disclosure can be produced by introducing the DNA or the recombinant vector of the present disclosure into a host.

In one or more embodiments, examples of the host include known microorganisms and cultured cells that are generally used. In one or more embodiments, examples of the microorganisms include *Escherichia coli* and yeast. In one or more embodiments, examples of the cultured cells include animal cells (e.g., CHO cells, HEK-293 cells, and COS cells) and insect cells (e.g., BmN4 cells).

Imaging Method

An aspect of the present disclosure relates to an imaging method using the fluorescent protein of the present disclosure, the DNA of the present disclosure, or the vector of the present disclosure. In one or more embodiments, the imaging method of the present disclosure includes introducing the fluorescent protein of the present disclosure into a cell or the like, turning on/off the fluorescence by photo-switching the fluorescent protein of the present disclosure, and/or detecting the fluorescence signals of the fluorescent protein of the present disclosure. In one or more embodiments, the imaging method of the present disclosure is super-resolution imaging. In one or more embodiments, examples thereof include PALM (photoactivated localization microscopy), STORM (stochastic optical reconstruction microscopy), RESOLFT (reversible saturable optical fluorescence transition), and SOFI (stochastic optical fluctuation imaging).

In one or more embodiments, in the case of using a negative photo-switchable type (e.g., Dronpa and rsEGFP) that switches from a non-fluorescent state to a fluorescent state by being irradiated with light having a specific wavelength that does not cause fluorescence excitation and switches from a fluorescent state to a non-fluorescent state by being irradiated with light for fluorescence excitation in the super-resolution imaging with RESOLFT, three types of light in total, namely doughnut light and normal light of 488 nm and normal light of 405 nm, are needed, and thus the optical system becomes complicated. On the other hand, in the case of using the fluorescent protein of the present disclosure, which is a positive photo-switchable type that switches from a non-fluorescent state to a fluorescent state by being irradiated with light for fluorescence excitation and switches from a fluorescent state to a non-fluorescent state by being irradiated with light having a specific wavelength that does not cause fluorescence excitation, only two types of light, namely normal light of 488 nm and doughnut light of 405 nm, are needed, and therefore, there is an advantage that the optical system is simple.

Moreover, in the case of the negative photo-switchable type, the fluorescence is switched off by the irradiation with excitation light for fluorescence observation, and therefore, a problem arises in that the fluorescence is switched off during the fluorescence observation and in that it is difficult to rapidly switch the fluorescence while a high S/N ratio is maintained.

Photochromic Material

The fluorescent protein of the present disclosure has a photochromism effect and thus can be used as a photochromic material applicable to optical recording media such as a CD, a DVD, a holographic recording medium and a smart card; display elements such as a billboard, a fluorescent plate, a TV, and a computer monitor; a lens; a biosensor; a biochip; a photochromic fiber material, and the like.

The present disclosure further relates to one or more embodiments below, but is not limited thereto.

[1] A fluorescent protein indicated in (a) or (b) below.
(a) A protein having an amino acid sequence of Sequence ID No. 1.
(b) A protein that has an amino acid sequence of Sequence ID No. 1 in which one to several amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

[2] A fluorescent protein according to [1], wherein the protein indicated in (b) above is a protein expressed in a fluorescent state.

[3] A fusion protein to which the fluorescent protein according to [1] or [2] is fused, and in which the fluorescent protein moiety can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

[4] The fusion protein according to [3], wherein the fluorescent protein moiety is expressed in a fluorescent state.

[5] DNA having a base sequence coding for the protein according to any of [1] to [4].

[6] DNA indicated in (c) or (d) below.
(c) A DNA having a base sequence of Sequence ID No. 3.
(d) A DNA having a base sequence of Sequence ID No. 3 in which one to several amino acids are deleted, substituted, and/or added, the base sequence coding for a protein that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

[7] The DNA according to [6], wherein the protein indicated in (d) above is expressed in a fluorescent state.

[8] A vector allowing the protein according to any of [1] to [4] to be expressed.

[9] A vector including the DNA according to any of [5] to [7].

[10] A transformant expressing the protein according to any of [1] to [4].

[11] An imaging method using the protein according to any of [1] to [4], the DNA according to any of [5] to [7], the vector according to [8] or [9], or the transformant according to [10].

[12] A photochromic material including the fluorescent protein according to any of [1] to [4].

Hereinafter, the present disclosure will be described more specifically by way of working examples, but these are merely examples, and the present disclosure is not limited to these working examples.

EXAMPLES

Production of Fluorescent Protein of Example 1

A fluorescent protein (fluorescent protein of Example 1) represented by the amino acid sequence of Sequence ID No. 1 was produced by introducing seven mutations, namely N102I, L141P, F173S, S190D, D192V, K202R, and E218G, into Padron (having an amino acid sequence of Sequence ID No. 2), which is a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

Production of Bacterial Expression Vector

A bacterial expression vector for the fluorescent protein of Example 1 was produced by introducing a gene (having a base sequence of Sequence ID No. 3) coding for the fluorescent protein of Example 1 into a bacterial expression vector pRSETB. Similarly, with respect to four reversibly photo-switchable fluorescent proteins, namely Padron, Dreiklang, rsEGFP and Dronpa, bacterial expression vectors were produced.

Production of Mammalian Expression Vector

A mammalian expression vector for the fluorescent protein of Example 1 was produced by introducing a gene (having a base sequence of Sequence ID No. 3) coding for the fluorescent protein of Example 1 into a mammalian expression vector pcDNA3.

A mammalian expression vector for the fluorescent protein of Example 1 to which a signal sequence or a signal protein below was fused was also produced. Specifically, 1) a redundant mitochondrial targeting signal derived from a precursor of a subunit VIII (COX-VIII) of human cytochrome c oxidase, 2) a Golgi body localization signal sequence of β-N-acetylglucosaminyl-glycopeptide β-1,4-galactosyl transferase, 3) a DNA binding protein, H2B, and 4) a nucleolus protein, fibrillarin, were fused to the fluorescent protein of Example 1 in order to cause the fluorescent protein of Example 1 to target a mitochondrion, a Golgi body, a nucleus, and a nucleolus, respectively.

Furthermore, mammalian expression vectors for fusion proteins in which β-actin, vimentin, paxillin, and zyxin were fused via a 17-amino acid linker sequence (GGSGGSGGSGGSGGQFQ) (SEQ ID No. 4) to the fluorescent protein of Example 1 were produced. Similarly, a mammalian expression vector for a fusion protein in which clathrin was fused via a 15-amino acid linker sequence to the fluorescent protein of Example 1 was also produced.

Purification of Fluorescent Protein of Example 1

The fluorescent protein of Example 1 having a polyhistidine tag at the N terminus was introduced into the bacterial expression vector pRSETB and was expressed in *Escherichia coli*. After being cultured in an LB medium at 23° C. for 65 hours, the cells were homogenized by French-press. The supernatant was purified by using a Ni-NTA agarose affinity column (available from Qiagen) followed by a gel filtration using a PD-10 column (available from GE Healthcare), and purified again using an AKTA 10S (GE Healthcare) Hi-load 20/60 Superdex 200 pg column.

Characterization of Fluorescent Protein of Example 1

The fluorescent protein of Example 1 was photo-switched on and off by LED light sources of 475±28 nm and 386±23 nm, respectively. An absorption spectrum was measured using a V-630 BIO spectrophotometer (available from JASCO). A fluorescent excitation spectrum and a fluorescent emission spectrum were measured using a F-7000 fluorescence spectrophotometer (available from Hitachi). Molar absorption coefficients were calculated using an absorbance of a purified protein of a known concentration measured by Bradford assay. Absolute fluorescence quantum yield was measured using Quantaurus QY-C11347 (available from Hamamatsu Photonics). In this measurement, the absorbance of the protein was adjusted to be less than 0.05. All of the above-mentioned measurements were performed using the protein in 20 mM HEPES buffer under a physiological pH condition.

The quantum yield of photoinduced on/off was calculated by measuring the irradiation-dependent change in the absorbance using a V-630 BIO spectrophotometer (available from JASCO). Specifically, the calculation was performed in accordance with the method described in Gayda, S., Nienhaus, K. & Nienhaus, G. U. Biophysical journal 103, 2521-31(2012).

In the measurement of the thermal relaxation time from the turning-off to the turning-on of the fluorescence, the fluorescence of 10 ml of 20 μM protein solution (20 mM HEPES buffer, pH 7.4) was turned off with light having a wavelength of 405 nm prior to the measurement, and then the fluorescence spectrum was measured.

Figures 1, 2:
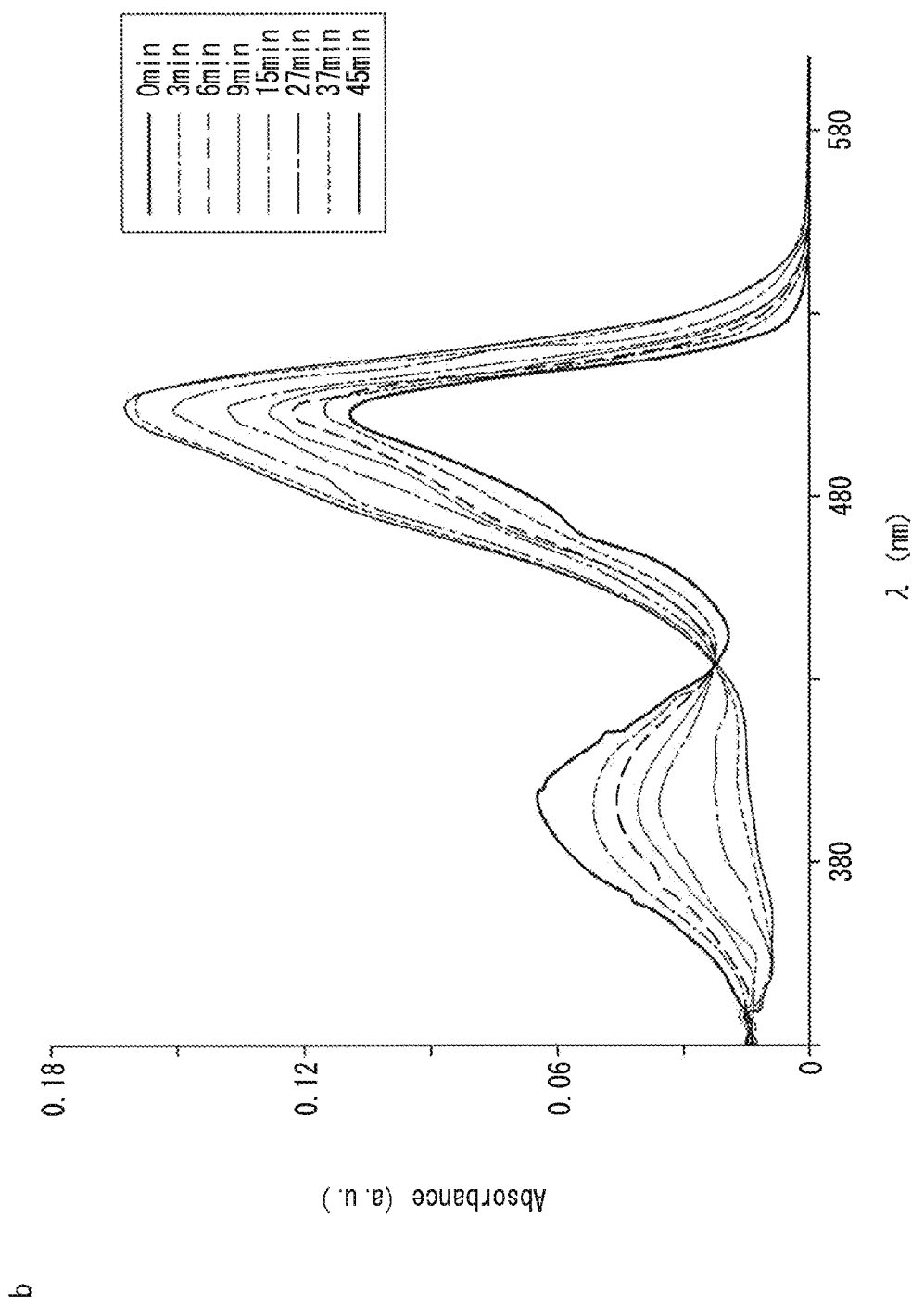
Figure 1:
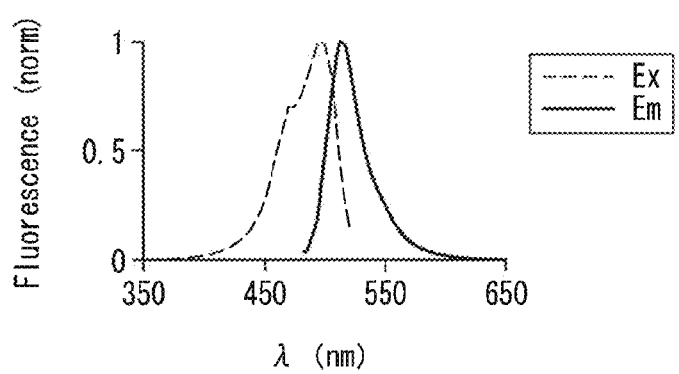
Figure 2:
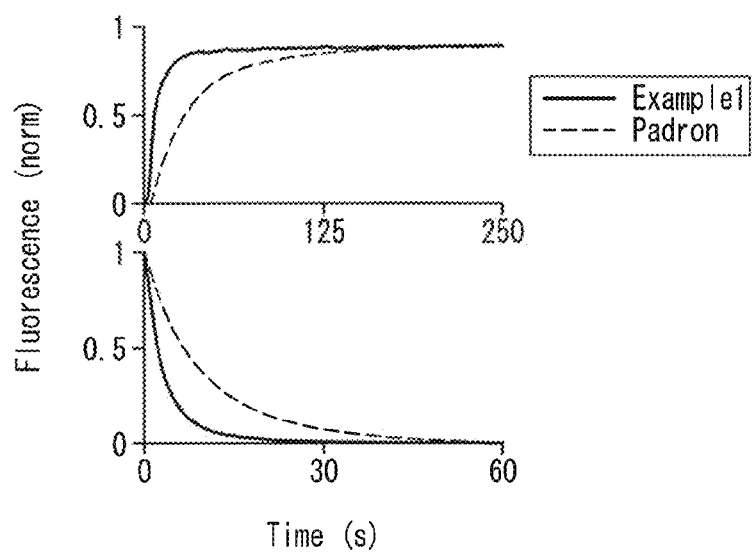
Figure 3:
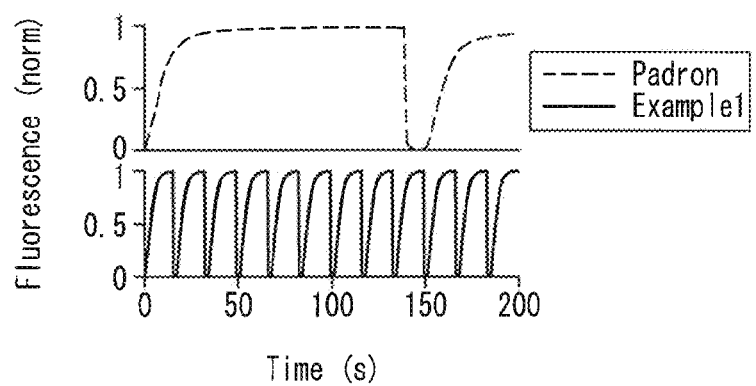
Figure 2:
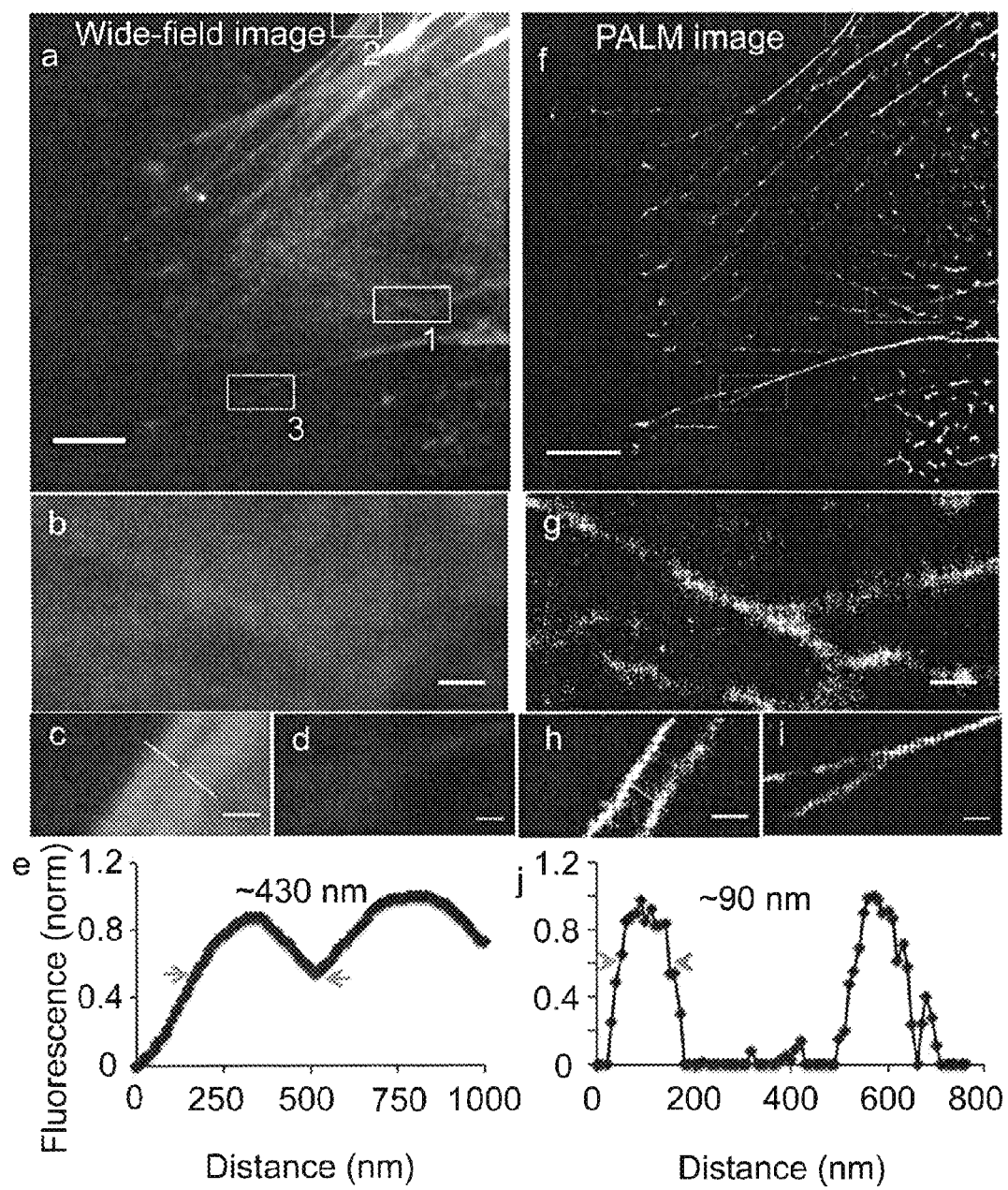

FIG. 1-1 to FIG. 2 and Table 1 to Table 3 show the results of the above-mentioned measurements.

TABLE 1

| RSFP | Maximum absorption wavelength (nm) | | Maximum excitation wavelength (nm) | Maximum fluorescence wavelength (nm) | Quantum yield QY | Molar absorption coefficient ($M^{-1}$ $cm^{-1}$) | Relaxation time ($t_{1/2}$), min |
|---|---|---|---|---|---|---|---|
| Example 1 | 495[a1] | 386[b1] | 495 | 514 | 0.67[c] | 30000 (on) 95000 (off) | 51 |
| Padron | 503[a1] | 396[b1] | 504 | 520 | 0.58[c] | 46000 | 180 |
| Dronpa | 503[a2] | 392[b2] | 503 | 522 | 0.68[c] | 98000 | 840 |
| rsEGFP | 493[a2] | 396[b2] | 493 | 510 | 0.36 | 47000 | 23 |

[a1]Absorption peak in switch-on and switch-off states.
[a2]Absorption peak in switch-on state.
[b1]Absorption peak in switch-on state.
[b2]Absorption peak in switch-off state.
[c]Absolute quantum yield (it should be noted that the quantum yields in Table 1 were measured in the switch-on state.)

TABLE 2

| | Fading half-life ($t_{1/2}$), sec | |
|---|---|---|
| RSFP | E. coli | Purified protein |
| Example 1 | 652 | 650 |
| Padron | 482 | 525 |
| Dreiklang | 315 | 387 |
| rsEGFP | 244 | 215 |
| Dronpa | 126 | 129 |

TABLE 3

| RSFP | Quantum yield, switch-on | Quantum yield, switch-off | Switching cycle (50% color fading) | Fading per cycle (%) | Switch-on time ($t_{1/2}$), sec | Switch-off time ($t_{1/2}$), sec |
| --- | --- | --- | --- | --- | --- | --- |
| Example 1 | 0.00837 | 0.0716 | 300 or less | 0.1 | 7.9 | 3.1 |
| Padron | 0.00232 | 0.0192 | 11 or less | 2.5 | 32.4 | 10.1 |

FIG. 1-1 to FIG. 1-4 are diagrams illustrating examples of characterization results of a fluorescent protein of Example 1. FIG. 1-1a and FIG. 1-2b show changes in irradiation-dependent absorbance spectra of the fluorescent protein of Example 1 (a) and Padron (b) at pH 7.4. FIG. 1-3c shows a fluorescent emission spectrum and an excitation spectrum of the fluorescent protein of Example 1. FIG. 1-3d shows kinetics of photo-switching on/off of the fluorescent protein of Example 1 and Padron. FIG. 1-3e shows examples of continuous photo-switching of the fluorescent protein of Example 1 and Padron. FIG. 1-4f shows examples of photobleaching kinetics of the fluorescent protein of Example 1, Padron, Dreiklang, rsEGFP, and Dronpa. Regarding the photobleaching of the protein of Example 1 and Dreiklang, a 488-nm laser beam (7.1 kW/cm$^2$) was applied, and the fluorescence was recorded. Regarding the photobleaching of rsEGFP and Dronpa, a 405-nm laser beam (29.1 kW/cm$^2$) as well as a 488-nm laser beam (7.1 kW/cm$^2$) were applied, and the fluorescence was recorded. FIG. 1-4g shows examples of photobleaching promoted by photo-switching.

In contrast with Padron having a quantum yield of 0.58, the fluorescent protein of Example 1 emitted bright fluorescence having a quantum yield of 0.67 in the fluorescent state (Table 1). The fluorescent protein of Example 1 showed two absorption peaks at 386 nm and 495 nm in the state in which the fluorescence was turned on and a single absorption peak at 495 nm in the state in which the fluorescence was turned off (FIG. 1-1a). The absorption at 495 nm contributes to both the photo-switching to the on-state and the excitation of a chromophore, resulting in the fluorescence emission at 514 nm (FIG. 1-3c). When the fluorescent protein of Example 1 in the fluorescent state was irradiated with light of 405 nm, the fluorescent protein switched to a non-fluorescent dark state with 2 to 3% fluorescence compared with the initial state (data not shown). The fluorescence of the fluorescent protein of Example 1 could be repeatedly turned on and off by the irradiation with light of 488 nm and 405 nm. The fluorescent protein of Example 1 was expressed in a fluorescent state, and on the other hand, Padron was expressed in a non-fluorescent state (data not shown). The thermal relaxation half-life of the fluorescent protein of Example 1 was 51 minutes (Table 1). The chromophore of the fluorescent protein of Example 1 maturated in a half-life $t_{1/2}$ of 20 minutes at 37° C. (data not shown). It was confirmed from the results of the size exclusion chromatography showing a single sharp peak that the fluorescent protein of Example 1 had the characteristic of a monomer (data not shown).

Photo-Switching Speed

The photo-switching properties of the fluorescent protein of Example 1 were compared with those of Padron, which is a counterpart of the fluorescent protein. Regarding the fluorescence turning-on kinetics, the fluorescence of both of the proteins was completely turned off at 405 nm (47 kW/cm$^2$) and then turned on using a 488-nm laser beam (95 kW/cm$^2$). The half-life ($t_{1/2}$) of switching of the fluorescence from an off state to an on state of the fluorescent protein of Example 1 was 7.9 seconds, and that of Padron was 32.4 seconds (Table 3, FIG. 1-3d). The half-life ($t_{1/2}$) of switching of the fluorescence from an on state to an off state of the fluorescent protein of Example 1 was 3.1 seconds, and that of Padron was 10.1 seconds (Table 3). Moreover, the time required for the complete photo-switching of the fluorescent protein of Example 1 was 17 seconds, and that of Padron was 152 seconds (FIG. 1-3e).

Photostability

The photostability of the fluorescent protein of Example 1 was compared with that of Padron, Dreiklang, rsEGFP, and Dronpa. The fluorescent protein of Example 1 had the best photostability among these RSFPs. The fading half-life of the fluorescent protein of Example 1 was 650 seconds in the case of using *Escherichia coli* cells expressing the fluorescent protein and 652 seconds in the case of using the purified fluorescent protein (FIG. 1-4f, Table 2). On the other hand, the fading half-life of Padron was 525 seconds in the case of using *Escherichia coli* cells expressing Padron and 482 seconds in the case of using purified Padron (FIG. 1-4f, Table 2).

The quantum yields of the turning-on and turning-off of the fluorescence were calculated from absorption cross sections (488 nm and 405 nm) per cm$^2$, a photo-switching speed, and a light irradiation power density for turning on and off the fluorescence (400 μW/cm$^2$ at 488 nm and 250 μW/cm$^2$ at 405 nm). The quantum yields of the turning-on and turning-off of the fluorescence of the fluorescent protein of Example 1 were 0.0084 and 0.0716, respectively. On the other hand, the quantum yields of the turning-on and turning-off of the fluorescence of Padron were 0.0023 and 0.019, respectively (Table 3).

With respect to the photobleaching promoted by photo-switching at pH 7.4, the purified fluorescent protein of Example 1 and Padron were compared with each other. In the fluorescent protein of Example 1, the color very slowly faded by 0.1% for each of the continuous photo-switching cycles (Table 3). On the other hand, in Padron, the color faded by 2.5% under the same conditions (Table 3).

Number of Photo-Switching Cycles

Due to an improvement in the speed of the turning on/off of the fluorescence and an improvement in the photostability in the fluorescent protein of Example 1, the number of photo-switching cycles increased. Specifically, until the fluorescence intensity decreased to 50%, the number of photo-switching cycles of Padron was 11, whereas that of the fluorescent protein of Example 1 was 290 (FIG. 1-4g, Table 3).

Super-Resolution Imaging Using PALM

A fusion protein of the fluorescent protein of Example 1 and β-actin was expressed in HeLa cells, and PALM (photoactivated localization microscopy) imaging was performed. A wide-field epi-illumination microscope equipped with a sCMOS camera was used for data collection. 5000 to 8000 images were collected in order to obtain a high resolution structure. The following is a specific method. FIG. 2 shows the results.

Cells to be used for the PALM imaging were subjected to transient transfection using lipofection at 40 to 50% confluency. The cells were fixed for 15 minutes using 2% (W/V)

paraformaldehyde 36 to 48 hours after the transfection. The fixed cells were mounted on slide glass for a microscope using Gelvatol fixing liquid.

The super-resolution imaging was performed using an inverted microscope (Ti-E available from Nikon) that was equipped with an APO TIRF 100× oil-immersion objective lens with a numerical aperture of 1.49, 405-nm and 488-nm lasers, a high-speed motor scanning stage (MLS203P2 available from Thorlabs), and a sCMOS camera (ORCA Flash 4.0 available from Hamamatsu Photonics), and that was controlled by a TIRF-system manufactured in-house.

FIG. 2 shows examples of PALM imaging results of HeLa cells expressing a fusion protein of the fluorescent protein of Example 1 and β-actin. FIG. 2a is a wide-field image of the fusion protein. FIGS. 2b, 2c, and 2d are enlarged views of boxes 1, 2, and 3 in FIG. 2a, respectively. FIG. 2e is a fluorescence line profile normalized along a solid line in FIG. 2c. FIG. 2f is a PALM image of the fusion protein. FIGS. 2g, 2h, and 2j are enlarged views of portions in FIG. 2f that correspond to boxes 1, 2, and 3 in FIG. 2a. FIG. 2j is a fluorescence line profile normalized along a solid line in FIG. 2h. Scale bars in FIGS. 2a and 2f indicate 5 μm. All scale bars in the enlarged views indicate 500 nm.

SEQUENCE LISTING FREE TEXT

SEQ ID No. 1: An embodiment of an amino acid sequence of the fluorescent protein of Example 1
SEQ ID No. 2: An amino acid sequence of Padron
SEQ ID No. 3: An embodiment of a base sequence coding for the fluorescent protein of Example 1
SEQ ID No. 4: A 17-amino acid linker sequence

---

The invention claimed is:

1. A fluorescent protein which is:
   (a) a protein having the amino acid sequence of SEQ ID No: 1; or
   (b) a protein that has the amino acid sequence of SEQ ID NO: 1 in which one to six amino acids are deleted, substituted, and/or added, and that can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

2. The fluorescent protein according to claim 1, wherein the protein indicated in (b) is a protein expressed in a fluorescent state.

3. A fusion protein to which the fluorescent protein according to claim 1 is fused, and in which a fluorescent protein moiety can serve as a fluorescent protein that switches from a non-fluorescent state to a fluorescent state by being irradiated with light for fluorescence excitation and switches from a fluorescent state to a non-fluorescent state by being irradiated with light having a specific wavelength that does not cause fluorescence excitation.

4. The fusion protein according to claim 3, wherein the fluorescent protein moiety is expressed in a fluorescent state.

5. An imaging method, comprising introducing the protein according to claim 3 into a cell, and detecting fluorescence signals of the protein.

6. The imaging method of according to claim 5, further comprising turning on/off fluorescence by photo-switching the protein.

* * * * *